(12) United States Patent
Zealear

(10) Patent No.: US 8,065,014 B2
(45) Date of Patent: Nov. 22, 2011

(54) METHOD FOR PROMOTING SELECTIVE REINNERVATION OF DENERVATED TISSUE

(75) Inventor: David L. Zealear, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 620 days.

(21) Appl. No.: 10/480,227

(22) PCT Filed: Jun. 21, 2002

(86) PCT No.: PCT/US02/19980
§ 371 (c)(1),
(2), (4) Date: Jun. 14, 2004

(87) PCT Pub. No.: WO03/000338
PCT Pub. Date: Jan. 3, 2003

(65) Prior Publication Data
US 2004/0215290 A1    Oct. 28, 2004

(51) Int. Cl.
*A61N 1/18* (2006.01)
*A61N 2/00* (2006.01)
(52) U.S. Cl. .......................................... 607/48; 607/50
(58) Field of Classification Search .................. 607/1, 2, 607/48, 50, 115, 116, 118, 134, 46; 600/9–15
See application file for complete search history.

(56) References Cited

U.S. PATENT DOCUMENTS

| | | | | |
|---|---|---|---|---|
| 3,893,462 A | * | 7/1975 | Manning | ........................ 607/51 |
| 4,155,353 A | | 5/1979 | Rea et al. | |
| 4,308,868 A | * | 1/1982 | Jhabvala | .......................... 607/50 |
| 4,774,967 A | * | 10/1988 | Zanakis et al. | ................ 606/152 |
| 4,907,602 A | | 3/1990 | Sanders | |
| 4,919,140 A | * | 4/1990 | Borgens et al. | ................. 607/50 |
| 5,016,647 A | * | 5/1991 | Sanders | .......................... 607/72 |
| 5,030,225 A | * | 7/1991 | Aebischer et al. | ............. 606/152 |
| 5,092,871 A | * | 3/1992 | Aebischer et al. | ............. 606/152 |
| 5,111,814 A | * | 5/1992 | Goldfarb | .......................... 607/48 |
| 5,133,354 A | | 7/1992 | Kallok | |
| 5,178,145 A | | 1/1993 | Rea | |
| 5,314,457 A | * | 5/1994 | Jeutter et al. | .................. 607/116 |
| 5,366,493 A | | 11/1994 | Scheiner et al. | |
| 5,433,735 A | * | 7/1995 | Zanakis et al. | .................. 607/50 |
| 5,480,416 A | | 1/1996 | Garcia et al. | |
| 5,504,197 A | | 4/1996 | Schubert et al. | |
| 5,562,707 A | | 10/1996 | Prochazka et al. | |

(Continued)

FOREIGN PATENT DOCUMENTS

WO    WO 97/15349    5/1997

(Continued)

OTHER PUBLICATIONS

Zealer et al. "Technical approach for reanimation of the chronically denervated larynx by means of functional electrical stimulation." Ann Otol Rhinol Laryngol. Sep. 1994; 103(9): 705-12.*

(Continued)

*Primary Examiner* — Carl H Layno
*Assistant Examiner* — Luther Behringer
(74) *Attorney, Agent, or Firm* — Jenkins, Wilson, Taylor & Hunt, P.A.

(57) ABSTRACT

A method for promoting reinnervation via stimulation of a denervated target tissue, whereby reinnervation of the target tissue by native neurons is enhanced, and whereby reinnervation of the target tissue by foreign neurons is inhibited.

21 Claims, 5 Drawing Sheets

U.S. PATENT DOCUMENTS

| | | | |
|---|---|---|---|
| 5,571,148 A | 11/1996 | Loeb et al. | |
| 5,584,290 A | 12/1996 | Brain | |
| 5,690,692 A | 11/1997 | Fleming | |
| 5,721,243 A | 2/1998 | Efange et al. | |
| 5,725,564 A * | 3/1998 | Freed et al. | 607/72 |
| 5,806,522 A | 9/1998 | Katims | |
| 5,833,709 A | 11/1998 | Rise et al. | |
| 5,897,579 A * | 4/1999 | Sanders | 607/42 |
| 5,898,066 A | 4/1999 | Benowitz et al. | |
| 5,983,140 A | 11/1999 | Smith et al. | |
| 5,991,649 A | 11/1999 | Garfield et al. | |
| 6,029,090 A | 2/2000 | Herbst | |
| 6,051,017 A | 4/2000 | Loeb et al. | |
| 6,095,148 A * | 8/2000 | Shastri et al. | 128/898 |
| 6,123,658 A | 9/2000 | Schweighofer et al. | |
| 6,132,360 A * | 10/2000 | Halpern | 600/9 |
| 6,132,361 A | 10/2000 | Epstein et al. | |
| 6,132,387 A | 10/2000 | Gozani et al. | |
| 6,134,469 A | 10/2000 | Wietholt | |
| 6,163,725 A | 12/2000 | Peckham et al. | |
| 6,179,771 B1 | 1/2001 | Mueller | |
| 6,214,021 B1 | 4/2001 | Hadlock et al. | |
| 6,217,491 B1 | 4/2001 | Schiessl | |
| 6,226,552 B1 | 5/2001 | Staunton et al. | |
| 6,233,472 B1 | 5/2001 | Bennett et al. | |
| 6,243,607 B1 | 6/2001 | Mintchev et al. | |
| 6,365,149 B2 | 4/2002 | Vyakarnam et al. | |
| 6,484,053 B2 * | 11/2002 | Leelamanit et al. | 607/2 |
| 6,652,443 B1 * | 11/2003 | Struppler et al. | 600/9 |
| 6,937,904 B2 * | 8/2005 | Richmond et al. | 607/46 |
| 2001/0018547 A1 * | 8/2001 | Mechlenburg et al. | 600/15 |

FOREIGN PATENT DOCUMENTS

| | | |
|---|---|---|
| WO | WO 97/18854 | 5/1997 |
| WO | WO 99/24111 | 5/1999 |

OTHER PUBLICATIONS

Zealer et al. "The effects of chronic electrical stimulation on laryngeal muscle reinnervation." ORL J Otorhinolaryngol. Mar.-Apr. 2000; 62(2):87-95.*

Al-Majed et al. "Brief Electrical Stimulation Promotes the Speed and Accuracy of Motor Axonal Regeneration." Journal of Neuroscience, Apr. 2000, 20(s): 2602-2608.*

Notification of Transmittal of International Preliminary Examiner Report in corresponding PCT Application No. PCT/US02/19980 dated Dec. 5, 2003.

Notification of Transmittal of International Search Report for corresponding PCT Application No. PCT/US02/19980 dated Mar. 4, 2003.

Al-Majed et al., Brief Electrical Stimulation Promotes the Speed and Accuracy of Motor Axonal Regeneration, *The J. of Neuroscience* 20(7):2602-2608 (Apr. 1, 2000).

Brushart et al., Contributions of Pathway and Neuron to Preferential Motor Reinnervation, *The J. of Neuroscience* 18(21):8674-8681 (Nov. 1, 1998).

Evans, Challenges to Nerve Regeneration, *Seminars in Surgical Oncology* 19:312-318 (2000).

Gutmann et al., *The Effect of Galvanic Exercise on Denervated and Re-innervated Muscles in the Rabbit*, pp. 7-17 (1943).

Kanaya et al., Effect of Electrostimulation on Denervated Muscle, *Presented at the Third Congress of International Federation of Societies for Surgery of the Hand*, Tokyo, Japan Nov. 5, 1986.

Pototschnig et al., Electromyographic evaluation in vocal cord disorders, *Acta oto-rhino-laryngologica belg.* 51:99-104 (1997). (Presented at the Royal Belgian Society for Ear, Nose, Throat, Head and Neck Surgery, Dec. 1996, Brussels, Belgium).

Rushton, Functional Electrical Stimulation, *Physio. Meas.* 18:241-275 (1997).

Salerno et al., Electrophysiological Study of the Denervated Orbicularis Oculi Muscle in Dogs, *Presented at the 30th Annual University surgical Residents' Conference of the Society of University Surgeons*, San Antonio, Texas, Feb. 10, 1988.

Stoll et al., Nerve Injury, Axonal Degeneration of Neural Regeneration: Basic Insights, *Brain Pathology* 9:313-325 (1999).

Wu et al., Painful Neuromas: A Review of Treatment Modalities, *Annals of Plastic Surgery* 43(6):661-667 (Dec. 1999).

Zealear et al., The Effects of Chronic Electrical Stimulation on Laryngeal Muscle Physiology and Histochemistry, *ORL* 62:81-86 (2000).

Zealear et al., Electrical Stimulation of a Denervated Muscle Promotes Selective Reinnervation by Native Over Foreign Motoneurons, *J. Neurophysiol.* 87:2195-2199 (2002).

Wen et al., Study of contractile properties of the posterior cricoarytenoid muscle after delayed reinnervation, *Lin Chuang Er Bi Yan Hou Ke Za Zhi* 12(9):411-414 (Sep. 1998) (Abstract).

Peterson et al., Comparison of nerve banking techniques in delayed laryngeal reinnervation, *Ann Otol Rhinol Laryngol* 108(7.1):689-694 (Jul. 1999) (Abstract).

Van Lith-Bijl et al., Laryngeal abductor reinnervation with a phrenic nerve transfer after a 9-month delay, *Arch Otolaryngol Head Neck Surg* 124(4):393-398 (Apr. 1998) (Abstract).

Sercarz et al., Physiologic motion after laryngeal nerve reinnvervation: a new method, *Otolaryngol Head New Surg* 116(4):466-474 (Apr. 1997) (Abstract).

Van Lith-Bijl et al, Selective laryngeal reinnervation with separate phrenic and ansa cervicalis nerve transfers, *Arch Otolaryngol Head Neck Surg* 123(4):406-411 (Apr. 1997) (Abstract).

Zheng et al., Laryngeal reinnervation by nerve-muscle multipedicle transfer, *Zhonghua Er Bi Yan Hou Ke Za Zhi* 31(1):29-32 (1996) (Abstract).

Kawakita, Motor innervation of the guinea pig arytenoids muscle from the standpoint of the reinnervation process, *Nippon Jibiinkoka Gakkai Kaiho* 98(3):391-401 (Mar. 1995) (Abstract).

Rubio et al., Laryngeal reinnervation: transposition of neuromuscular pedicles, *Acta Otorrinolaringol Esp* 45(3):301-305 (Sep.-Oct. 1995) (Abstract).

Sanders et al., The innervation of the human posterior cricoarytenoid muscle evidence for at least two neuromuscular compartments, *Laryngoscope* 104(7):880-884 (Jul. 1994) (Abstract).

Doyle et al., Phrenic nerve reinnervation of the cat's larynx: a new technique with proven success, *Ann Otol Rhinol Laryngol* 102(11):837-842 (Nov. 1993) (Abstract).

Crumley, Endoscopic laser medical arytenoidectomy for airway management in bilateral laryngeal paralysis, *Ann Otol Rhinol Laryngol* 102(2):81-84 (Feb. 1993) (Abstract).

Liang, Reinnervation of posterior cricoarytenoid muscle: a comparsion of nerve implantation and neuromuscular pedicle transfer in an animal model, *Zhonghua Er Bi Yan Hou Ke Za Zhi* 28(1):19-21 (1993) (Abstract).

Green et al., Physiologic motion after vocal cord reinnervation: a preliminary study, *Laryngoscope* 102(1):14-22 (Jan. 1992) (Abstract).

Lewis et al., Does intralaryngeal motor nerve sprouting occur following unilateral recurrent laryngeal nerve paralysis? *Laryngoscope* 101(12.1):1259-1263 (Dec. 1991) (Abstract).

Crumley, Muscle transfer for laryngeal paralysis. Resotration of inspiratory vocal cord abduction by phrenic-omohyoid transfer, *Arch Otolaryngol Head Neck Surg* 117(10):1113-1117 (Oct. 1991) (Abstract).

Kano et al., Posterior cricoarytenoid muscle denervation, *Arch Otolaryngol Head Neck Surg* 117(9):1019-1020 (Sep. 1991) (Abstract).

Nahm et al., Regeneration of the recurrent laryngeal nerve in the guinea pig: reorganization of motoneurons after freezing injury, *Am J Otolaryngol* 11(2):90-98 (Mar.-Apr. 1990) (Abstract).

Jacobs et al., Reinnervation of the canine posterior cricoarytenoid muscle with sympathetic preganglionic neurons, *Ann Otol Rhinol Laryngol* 99(3.1):167-174 (Mar. 1990)(Abstract).

Maniglia et al., Newer technique of laryngeal reinnervation: superior laryngeal nerve (motor branch) as a driver of the posterior cricoarytenoid muscle, *Ann Otol Rhinol Laryngol* 98(11):907-909 (Nov. 1989) (Abstract).

Ducharme et al., Attempts to restore abduction of the paralyzed equine arytenoids cartilage. III. Nerve anastomosis, *Can J. Vet Res* 53(2):216-223 (Apr. 1989) (Abstract).

Crumley, Laryngeal synkinesis: its significance to the laryngologist, *Ann Otol Rhinol Laryngol* 98(2):87-92 (Feb. 1989) (Abstract).
Martin, Animal experiement studies of collateral reinnervation of denervated laryngeal musculature, *Laryngol Rhino Otol (Stuttg)* 68(1):57-61 Jan. 1989) (Abstract).
Maniglia et al., New techniques of laryngeal reinnervation, *Ann Otol Rhinol Laryngol* 98(1.1):8-14 (Jan. 1989) (Abstract).
Capella et al., Laryngeal reinnervation in the dog, *An Otorrinolaringol Ibero Am* 16(2):187-214 (1989) (Abstract).
Fata et al., Histochemical study of posterior cricoarytenoid muscle reinnervation by a nerve-muscle pedicle in the cat, *Ann Otol Rhinol Laryngol* 96(5):479-487 (Sep.-Oct. 1987) (Abstract).
Brondbo et al., *Experimental laryngeal reinnervation by phrenic nerve implantation into the posterior cricoarytenoid muscle, Acta Otolaryngol* 103(3-4):339-344 (Mar.-Apr. 1987) (Abstract).
May et al., Muscle-nerve pedicle laryngeal reinnervation, *Laryngoscope* 96(11):1196-11200 (Nov. 1986) (Abstract).
Brondbo et al., Functional results after experimental reinnervation of the posterior cricoarytenoid muscle in dogs, *J. Otolaryngol* 15(5):259-264 (Oct. 1986) (Abstract).
Gambino et al., Three-dimensional computer reconstruction of the neuromuscular junction distribution in the human posterior cricoarytenoid muscle, *Laryngoscope* 95(5):556-560 (May 1985) (Abstract).
Chang, Studies of early laryngeal reinnervation, *Laryngoscope* 95(4):455-457 (Apr. 1985) (Abstract).
Crumley, Phrenic nerve graft for bilateral vocal cord paralysis,*Laryngoscope* 93(4):425-428 (Apr. 1983) (Abstract).
Crumley, Experiments in laryngeal reinnervation, *Laryngoscope* 92(9.2 Supp 30):1-27 (Sep. 1982) (Abstract).
Tucker, Nerve-muscle pedicle reinnervation of the larynx:avoiding pitfalls and complications, *Ann Otol rhinol Laryngol* 91(4.1):440-444 (Jul.-Aug. 1982) (Abstract).
Neal et al., Delayed reinnervation of unilateral vocal cord paralysis in dogs, *Otolaryngol Head Neck Surg* 89(4):608-612 (Jul.-Aug. 1981) (Abstract).
Tucker, Reinnervation of the paralyzed larynx: a review, *Head Neck Surg* 1(3):235-242 (Jan.-Feb. 1979) (Abstract).
Tucker, Human laryngeal reinnervation, *Laryngoscope* 86(6):769-779 (Jun. 1976) (Abstract).
Weber, et al., Magnetic stimulation of the central and peripheral nervous systems, *Muscle Nerve* 25(2):160-175 (Feb. 2005) (Abstract).
Wassermann, et al., Therapeutic application of repetitive transcranial magnetic stimulation: a review, *Clin Neurophysiol* 112(8):1367-1377 (Aug. 2001) (Abstract).
Al-Majed et al., Brief electrical stimulation promotes the speed and accuracy of motor axonal regeneration, *J. Neurosci* 20(7):2602-2608 (Apr. 2000) (Abstract).
Wigston et al., The location of cues promoting selective reinnervation of axolotl muscles, *J. Neurosci* 8(9):3451-3458 (Sep. 1988) (Abstract).
Kanaya et al., Effect of electrostimulation on denervated muscle, *Clin Orthop* 283:296-301 (Oct. 1992) (Abstract).
Salerno et al., Blink reflex recovery after electrical stimulation of the reinnervation orbicularis oculi muscle in dogs, *Ann Plast Surg* 25(5):360-371 (Nov. 1990) (Abstract).
Filogamo et al., Models of neuronal plasticity and repair in the enteric nervous system: a review, *Ital J. Anat Embryol* 100(1):185-195 (1995) (Abstract).
Verdu et al, Influence of aging on peripheral nerve function and regeneration, *J. Peripher Nerv Syst* 5(4):191-208 (Dec. 2000) (Abstract).
Evans, Challenges to nerve regeneration, *Semin Surg Oncol* 19(3):312-318 (Oct.-Nov. 2000) (Abstract).
Zochodne et al., The microenvironment of injured and regenerating peripheral nerves, *Muscle Nerve* Suppl 9:S33-S38 (2000) (Abstract).
McGowan et al., Laminins and human disease, *Microsc Res Tech* 51(3):262-279 (Nov. 1, 2000) (Abstract).
Strand, David and Goliath—the slingshot that started the neuropeptide revolution, *Eur J. Pharmacol* 405(1-3):3-12 (Sep. 2000) (Abstract).

Di Giulio et al., Glycosaminoglycans co-administration enhance insulin-like growth factor-I neuroprotective and neuroregenerative activity in traumatic and genetic models of motor neeuron disease: a review, *Int J. Dev Neurosci* 18(4-5):339-346 (Jul.-Aug. 2000) (Abstract).
Pearson, Plasticity of neuronal networks in the spinal cord: modifications in response to altered sensory input, *Prog Brain Res* 128:61-70 (2000) (Abstract).
Wu et al>, Painful neuromas: a review of treatment modalities, *Ann Plast Surg* 43(6):661-667 (Dec. 1999) (Abstract).
Mariniello et al., En bloc resection of an intracavernous oculomotor nerve schwannoma and grafting of the oculomotor nerve with sural nerve. Case report and review of the literature, *J. Neurosurg* 91(6):1045-1049 (Dec. 1999) (Abstract).
Satou et al., Experimental studies on peripheral nerve repair: a possibility of application to cure nerve complication of Hansen's disease, *Nihon Hansenbyo Gakkai Zasshi* 68(2):77-82 (Jul. 1999) (Abstract).
de Gasparo et al., The AT2 receptor: fact, fancy and fantasy, *Regul Pept* 81(1-3):11-24 (May 1999) (Abstract).
Stoll et al., Nerve injury, axonal degernation and neural regeneration: basic insights, *Brain Pathol* 9(2):313-325 (Apr. 1999) (Abstract).
Sanes et al., Development of the vertebrate neuromuscular junction, *Annu Rev Neurosci* 22:389-442 (1999) (Abstract).
Hogervorst et al., Mechanoreceptors in joint function, *J Bone Joint Surg Am* 80(9):1365-1378 (Sep. 1998) (Abstract).
Rutishauser, Polysialic acid at the cell surface: biophysics in service of cell interactions and tissue plasticity, *J Cell Biochem* 70(3):304-312 (Sep. 1998) (Abstract).
Gorio et al., Neuroprotection, neuroregeneration, and interaction with insulin-like growth factor-I: novel non-anitcoagulant action of glycosaminoglycans, *J Neurosci Res* 51(5):559-562 (Mar. 1998) (Abstract).
Van Overbeeke et al., Intracranial repair of a divided trochlear nerve. Case report, *J Neurosurg* 88(2):336-339 (Feb. 1988) (Abstract).
Klimaschewski, VIP—a 'very important peptide' in the sympathetic nervous system? *Anat Embryol (Berl)* 196(4):269-277 (Oct. 1997) (Abstract).
Cheney et al., Trigeminal neo-neurotization of the paralyzed face, *Ann Otol Rhinol Laryngol* 106(9):733-738 (Sep. 1997) (Abstract).
Pototschnig et al, Electromyographic evaulation of vocal cord disorders, *Acta Otorhinolaryngol Belg* 51(2):99-104 (1997) (Abstract).
Doi, New reconstructive procedure for brachial plexus injury, *Clin Plast Surg* 24(1):75-85 (Jan. 1997) (Abstract).
Hall, The laminins, *Int J Biochem Cell Biol* 28(9):957-959 (Sep. 1996) (Abstract).
Carratu et al., Role of polysialic acid in peripheral myelinated axons, *Microsc Res Tech* 34(6):489-491 (Aug. 1996) (Abstract).
Wigston et al., The location of cures promoting selective reinnervation of axoloti muscles, *J Neurosci* 8(9):3451-3458 (Sep. 1988) (Abstract).
Politis, Tropic factors in reactive mammalian central nervous system tissue, *Brain Res* 328(2):277-281 (Mar. 1985) (Abstract).
Stanco et al., Agrin and acetylcholine receptor distribution following electrical stimulation, *Muscle Nerve* 21(3):407-409 (Mar. 1998) (Abstract).
Koltzenburg et al., Functional reinnervation of sweat glands in the adult cat paw by inappropriate postganglionic axons, *J Auton Nerv Syst* 60(3):193-199 (Sep. 1996) (Abstract).
Lewis et al., Effects of long-term phasic electrical stimulation on denervated solcus muscle: guinea-pig contrasted with rat, *J Muscle Res Cell Motil* 18(5):573-586 (Oct. 1997) (Abstract).
Salerno et al., Blink reflex recovery after electrical stimulation of the reinnervated orbicularis oculi muscle in dogs, *Ann Plast Surg* 25(5):360-371 (Nov. 1990 (Abstract).
Edstrom and Kugelberg, "Histochemical composition, distribution of fibres and fatiguability of single motor units. Anterior tibial muscle of the rat," J. Neurol. Neurosurg. Psychiatry, vol. 31, pp. 424-433 (1968).
Flynt et al., "Laryngeal Synkinesis Following Reinnervation in the Rat—Neuroanatomic and Physiologic Study Using Retrograde Fluorescent Tracers and Electromyography," Ann. Otol. Rhinol. Laryngol., vol. 100, pp. 797-806 (1999).

Hall, S., "Axonal Regeneration through Acellular Muscle Grafts," J. Anat., vol. 190, pp. 57-71 (1997).

Herzon et al., "Functional Electrical Stimulation in the Canine Larynx Controlled by Respiration for Reanimation of the Paralyzed Larynx," Otolaryngology—Head and Neck Surgery, vol. 111, No. 2, p. 121 (Aug. 1994). (Abstract).

Popovic et al., "Functional electrical stimulation for grasping and walking: indications and limitations," Spinal Cord, vol. 39, pp. 403-412 (2001).

Sanders et al., "Laryngeal Pacing with the Medtronic ITREL II," Otolaryngology—Head and Neck Surgery, vol. 111, No. 2, p. 121 (Aug. 1994). (Abstract).

Sweeney et al., "Finite state control of functional electrical stimulation for the rehabilitation of gait," Med. Biol. Eng. Comput., vol. 38, pp. 121-126 (2000).

Zealear et al., "Electrically stimulated glottal opening combined with adductor muscle botox blockade restores both ventilation and voice in a patient with bilateral laryngeal paralysis," The Annals of Otology, Rhinology, and Laryngology, vol. 111, No. 6, pp. 500-506 (2002).

Zealear et al., "Reanimation of the Paralyzed Human Larynx With an Implantable Electrical Stimulation Device," The Laryngoscope, vol. 113, No. 7, pp. 1149-1156 (Jul. 2003).

\* cited by examiner

METHOD FOR PROMOTING SELECTIVE REINNERVATION OF DENERVATED TISSUE

GRANT STATEMENT

This work was supported by the U.S. National Institute on Deafness and Other Communication Disorders Grant 2RO1 DC-01149 and under Grant No. DC008429 awarded by National Institutes of Health. Thus, the U.S. Government has certain rights in the invention.

RELATED APPLICATION INFORMATION

This application is based on and claims priority to U.S. Provisional Patent Application Ser. No. 60/299,962, filed Jun. 21, 2001, the entire contents of which are herein incorporated by reference.

FIELD OF THE INVENTION

The present invention generally relates to a method for reinnervation of a denervated target cell or tissue. More particularly, the present invention provides a method for promoting reinnervation of a denervated muscle in a subject by stimulation of the denervated muscle.

| Table of Abbreviations | |
|---|---|
| ΔGA | change in hemiglottal area |
| EEMG | evoked electromyography |
| EMG | electromyography |
| FES | functional electrical stimulation |
| GA | hemiglottal area |
| PCA | posterior cricoarytenoid |
| PMR | preferential motor regeneration |
| PPS | pulses per second |
| RGC | reflex glottic closure |
| RL | recurrent laryngeal |
| RLN | recurrent laryngeal nerve |
| RQI | Reinnervation Quality Index |
| SLN | superior laryngeal nerve |
| TA | thyroarytenoid |

BACKGROUND ART

Peripheral nerve injuries can result from mechanical, thermal, chemical, congenital, or pathological etiologies. Failure to restore these damaged nerves can lead to the loss of muscle function, impaired sensation, and painful neuropathies.

Under some circumstances, neurons are capable of regenerating axonal connections and reestablishing synaptic connections with a target tissue. If these connections are regained, considerable function can be restored. A substantial barrier to successful recovery of denervated tissue is the formation of both functional and appropriate connections.

Thus, there exists a long-felt need in the art for therapies that support functional restoration of denervated muscle. To meet such a need, the present invention provides a method for promoting functionally appropriate reinnervation of a denervated tissue by adult neurons. In particular, stimulation of a target tissue can induce specific reconnection of neurons to the target tissue.

SUMMARY OF INVENTION

The present invention discloses a method for promoting reinnervation of a denervated target cell or tissue in a subject comprising stimulating a denervated target tissue, whereby reinnervation of the target tissue by native neurons is enhanced, and whereby reinnervation of the target tissue by foreign neurons is inhibited. In one embodiment of the invention, the native neurons comprise motoneurons and the foreign neurons also comprise motoneurons.

The stimulation can comprise electrical or magnetic stimulation and can be provided continuously or intermittently. Preferably, the stimulating comprises stimulating the target tissue, wherein a pattern of stimulatory activity in the target tissue is substantially similar to an endogenous pattern of stimulatory activity in the target tissue prior to denervation.

In one embodiment of the invention, a denervated target cell or tissue is stimulated using a stimulator device in proximity to a denervated muscle. Optionally, a stimulator device to be used in accordance with the disclosed method can be implantable or injectable. Preferably, a stimulator device is programmable such that the provision of stimulation is predictably controlled.

In a preferred embodiment, the methods of the present invention can be used to promote reinnervation of a denervated muscle including but not limited to a smooth muscle, a cardiac muscle, or a skeletal muscle. In a more preferred embodiment, the disclosed method is used to promote reinnervation of a denervated laryngeal muscle, such as a posterior cricoarytenoid muscle.

Reinnervation resulting from performance of the disclosed method comprises reformation of functional neuronal connections in a denervated muscle. Preferably, the method further comprises stimulating the denervated target tissue, whereby function of the tissue is restored. For example, the method can comprise stimulating the muscle, whereby contraction of the muscle is restored.

Accordingly, it is an object of the present invention to provide a method for promoting reinnervation of a denervated target tissue. This object is achieved in whole or in part by the present invention.

An object of the invention having been stated above, other objects and advantages of the present invention will become apparent to those skilled in the art after a study of the following description of the invention and nonlimiting Examples.

BRIEF DESCRIPTION OF THE DRAWINGS

FIG. 1A is a schematic drawing of laryngeal anatomy.

FIG. 1B depicts movement of the laryngeal muscle during inspiration. Inspiratory motor units in the recurrent laryngeal (RL) nerve and posterior cricoarytenoid (PCA) muscle are recruited during hypercapnea to abduct the vocal fold and open the airway. The direction of movement by the PCA muscles is indicated by arrows.

FIG. 1C depicts the movement of laryngeal muscles during airway closure. For the normally innervated larynx, stimulation of afferents in the superior laryngeal nerve (internal branch) reflexly activate reflex glottic closure (RGC) motor units in the RL nerve and thyroarytenoid (TA) muscle to adduct the vocal fold and close the airway. The direction of movement by the TA muscles is indicated by arrows.

FIG. 2A is a recording of inspiratory activity at the beginning of $CO_2$/air delivery.

FIG. 2B is an evoked electromyograph (EEMG) following recurrent laryngeal (RL) nerve stimulation.

FIG. 2C is an EEMG following inadvertent stimulation of the RL nerve motor fibers within the vagus nerve just posterior to the superior laryngeal nerve.

FIG. 2D is a recording of RGC motor units activated polysynaptically via superior laryngeal nerve stimulation.

DETAILED DESCRIPTION OF THE INVENTION

I. General Considerations

Figure 1A:
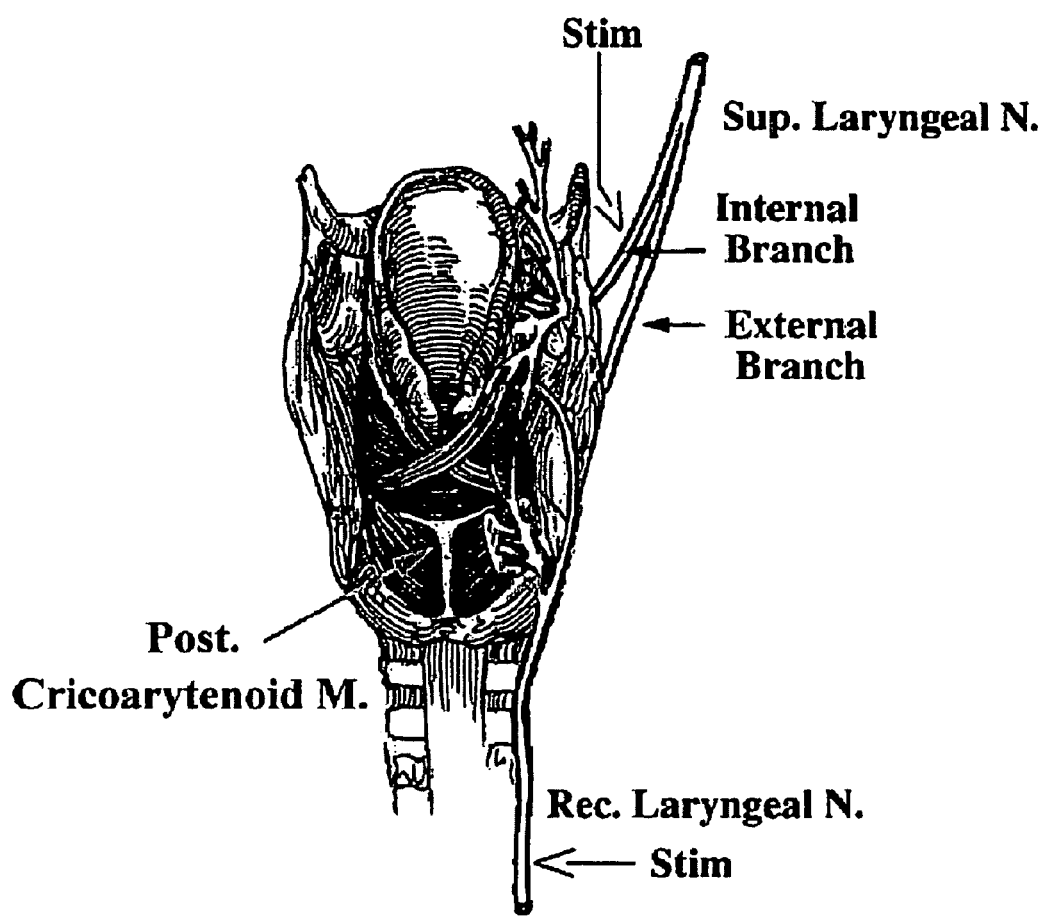
FIGS. 1A-1C are schematic drawings of laryngeal anatomy and muscle actions.

The methods of the present invention can be used to promote reinnervation by neurons capable of regeneration following denervation of a target tissue. The method involves the stimulating a target tissue to promote selective reinnervation of functionally appropriate connections. Related studies have described the beneficial effects of neurotrophic factors in promoting nerve growth and stimulation of muscle to restore-contractility to atrophied muscle, as summarized herein below. However, prior to the disclosure herein, induction of specific motoneuron-muscle reconnection by stimulation has not been described.

The relationship between neurons and an innervated target tissue is reciprocally supportive. Neuronal disease or injury can lead to atrophy of the target tissue, and conversely, target tissue disease or injury can impair the function of innervating neurons.

Diffusable factors (e.g., tropic and/or trophic factors) can influence neural connectivity during development and following injury or disease. Diffusable factors have been invoked to explain attraction of regenerating central nerve fibers (Politis, 1985). Previous studies also suggest that distal stumps of transected peripheral nerves contain diffusible factors that can attract/support axonal regeneration.

The term "preferential motor regeneration" or "PMR" is used to refer to a regenerating motoneuron's preference for a motor versus skin pathway. Collaterals of single motor axons often regenerate down both sensory and motor pathways at a nerve bifurcation. Subsequently, the collaterals in the sensory pathway are pruned, while those in the motor pathway are maintained (Brushart et al., 1998). This process is thought to be directed by neurotropins acting on motor neuron cell bodies in the spinal cord. In an animal model, resection of the target muscle had a minimal effect on PMR, supporting the notion that PMR is the result of central rather than target processes (Brushart et al., 1998).

In the same animal model for PMR, brief electrical stimulation of motoneurons above the site of injury can increase the speed of motoneuron regeneration and the degree of pathway preference (Al-Majed et al., 2000). These results are also consistent with a central influence on axonal regrowth toward a target tissue.

In contrast to the above-referenced studies, the present invention pertains to the pattern of reconnection of neurons within a target tissue. The disclosure of the present invention reveals that a neurotrophic effect alone is inadequate to elicit selective reinnervation, i.e. where reinnervation of the target tissue by native neurons is enhanced, and where reinnervation of the target tissue by foreign neurons is inhibited. Rather, reinnervation specificity was conferred only when the target tissue was electrically activated.

Functional electrical stimulation (FES) refers to electrical stimulation that is used to replace lost or damaged functions. Devices delivering FES include a type of neural prosthesis that substitutes for a damaged or destroyed neural function. For example, in cases of muscle atrophy resulting from disuse or paralysis, an increase in contractility with electrotherapy can allow performance of muscle functions despite weakened motor command signals from the brain. See e.g., Rushton (1997) *Physiol Meas* 18:241-275; Popovic et al. (2001) *Spinal Cord* 39:403-412; Sweeney et al. (2000) *Med Biol Eng Comput* 38:121-126; Gorman (2000) *Neurorehabil Neural Repair* 14:251-263; U.S. Pat. Nos. 5,725,564 and 5,897,579; and PCT International Publication Nos. WO 97/15349 and WO 99/24111. In contrast to the methods of the present invention, FES as described in the above-noted references constitutes replacement of endogenous neural functions with a stimulator device, and no recovery of endogenous neural functions is described.

Functional electrical stimulation of muscle to promote muscle restoration of endogenous neural functions has been explored (Zealear et al., 2000a; Zealear et al., 2000b), although the beneficial effect of such stimulation treatment in promoting reformation of neuronal connections remains controversial. In particular, concerns have been raised to suggest that early application of electrical stimulation might interrupt the natural course of reinnervation and the potential for spontaneous recovery.

A preliminary study indicated that muscle stimulation causes an overall repression of reinnervation (Zealear et al., 2000a). This observation suggested two contrary results. In one instance, muscle stimulation might repress reinnervation of both native and foreign neurons and thus have deleterious effects on recovery of muscle function. Alternatively, repression of reinnervation by foreign neurons, in the absence of similar repression of native neuron reinnervation, would promote functional recovery of the muscle. The disclosure of the present invention establishes, for the first time, that muscle stimulation: (1) selectively interferes with reinnervation by foreign neurons; and (2) enhances reinnervation by native neurons.

II. Definitions

While the following terms are believed to be well understood by one of ordinary skill in the art, the following definitions are set forth to facilitate explanation of the invention.

The term "regenerate" generally refers to regrowth of a neuronal process, for example an axon, following damage or loss of the same. Regeneration can occur in the absence of reinnervation.

The term "reinnervation" refers to reformation of a functional neuronal connection following denervation.

Conversely, the term "denervation" refers to a disconnection of neurons from a target tissue. Thus, a "denervated" target tissue refers to a target tissue that has been disconnected from its neurons to an extent that function of the target tissue is substantially lost. For example, a "denervated" muscle describes a muscle to which neuronal connections have been severed by injury or disease, to thereby reduce or eliminate an ability of the muscle to contract in response to endogenous stimuli.

The term "functional neuronal connection" or "functional connection" refers to a synaptic connection, wherein a neuron or neuronal process contacts a target tissue, and wherein stimulation of the neuron can elicit a post-synaptic potential in the target tissue.

The term "selective reinnervation" refers to an increase in the percentage of appropriate functional neuronal connections in a denervated target tissue. Stated another way, the term "selective reinnervation" refers to an enhancement of reinnervation by native neurons coupled with an interference of reinnervation by foreign neurons. Thus, selective reinnervation refers to an enhancement of correct reinnervation and a suppression of incorrect reinnervation.

The term "native neuron" refers to a neuron that normally innervates a particular target tissue. Thus, the term "native neuron" includes an endogenous neuron innervating a target tissue whose process or axon has become disconnected from the target tissue during denervation and whose process can potentially re-establish connection to the target tissue following regeneration and process outgrowth. The term "native neuron" is also used herein to refer to neurons provided via nerve repair strategies, wherein the neurons can form correct neuronal connections to replace connections of native neurons.

The term "foreign neuron" refers to a neuron that can, but typically does not, innervate a particular target tissue. For example, a neuron that innervates a tissue in response to trauma, but otherwise does not innervate a same untraumatized tissue, is a foreign neuron.

Native and foreign neurons can be identified by distinguishing features including but not limited to position of a neuronal cell body, the origin of afferent inputs to the neuron, and the type of neurotransmitter released upon stimulation of the neuron.

The terms "correct" and "appropriate," as used herein to describe a quality of reinnervation, each refer to the formation of functional connections by native neurons. Thus, "correct reinnervation" and "appropriate reinnervation" each describes reinnervation that restores target tissue function to its pre-denervated function.

The terms "incorrect" and "inappropriate," as used herein to describe a quality of reinnervation, each refer to the formation of functional connections by foreign neurons. Thus, "incorrect reinnervation" and "inappropriate reinnervation" each describes reinnervation in the absence of functional restoration of the target tissue.

The term "target tissue" generally refers to a tissue with which a neuron is functionally connected, i.e. on which a neuron synapses. The term "target tissue" also refers to a cell in the target tissue. Representative target tissues include but are not limited to muscles (e.g., skeletal muscle, smooth muscle, and cardiac muscle), nervous tissue (including central nervous system neurons or peripheral nervous system neurons), and epithelia.

The term "stimulate" as used herein comprises any suitable method for evoking an action potential, including but not limited to provision of electrical stimulation, magnetic stimulation, or a combination thereof. The term "stimulate" also encompasses provision of a pharmacological agent that evokes an action potential.

The terms "a," "an," and "the" are used in accordance with long-standing convention to refer to one or more.

The term "about", as used herein when referring to a measurable value such as a magnitude of a stimulus, a frequency of stimulation, etc. is meant to encompass variations of ±20% or ±10%, more preferably ±5%, even more preferably ±1%, and still more preferably ±0.1% from the specified amount, as such variations are appropriate to perform a disclosed method or otherwise carry out the present invention.

III. Therapeutic Methods

The present invention provides a method for promoting selective reinnervation of a denervated target tissue in a subject comprising stimulating a denervated target tissue, whereby reinnervation of the target tissue by native neurons is enhanced, and whereby reinnervation of the target tissue by foreign neurons is inhibited. The present invention also encompasses stimulating reconnecting neurons within a target tissue.

The step of stimulating comprises providing an effective amount of stimulation, such as electrical stimulation or magnetic stimulation. The term "effective amount" is used herein to describe an amount of stimulation is sufficient to promote selective reinnervation of a target tissue. Preferably, reinnervation comprises an increase in appropriate functional connections, such that the target tissue function is restored. An effective amount can also be described as an amount sufficient to elicit a specified electrophysiological response in a target tissue.

Electrical or magnetic stimulation comprises a plurality of signals or pulses. Each signal can have a distinct shape such as a sine wave, a square wave, a sawtooth wave, a simple pulse, or a complex pulse. Thus, an effective amount of stimulation can be described in terms of pulse shape, pulse magnitude (e.g., milliamps), pulse period (e.g., milliseconds), pulse frequency (e.g., pulses per second), duration of the stimulation period, duty cycle (percentage of stimulus "on" relative to stimulus "off"), and combinations thereof.

In one embodiment of the invention, an effective amount of electrical or magnetic stimulation is administered in a magnitude, frequency, and duration that is similar to: (a) an amount of stimulation provided by endogenous neurons prior to denervation; or (b) an amount of stimulation provided by endogenous neurons to a similar nondenervated target tissue (e.g., a corresponding muscle on the contralateral side). For example, a slow contracting muscle such as the soleus muscle is innervated by nerve fibers that fire with a low frequency (less than or equal to about 10 pps), sustained, tonic type activity. To promote reinnervation by native slow type motoneurons, a denervated soleus muscle is preferably stimulated in a similar pattern of low frequency, tonic type activity with a long duty cycle. As another example, a fast contracting muscle such as the tibialis anterior muscle is innervated by nerve fibers that fire with a high frequency (greater than or equal to about 50 pps), transient, phasic type of activity. Thus, to promote reinnervation by native fast motoneurons, a denervated tibialis anterior muscle is preferably stimulated in a similar pattern of high frequency, phasic type activity with a short duty cycle.

Stimulus parameters that are effective for induction of selective reinnervation can be tailored to a particular muscle, including fast muscles and slow muscles, and to the physical characteristics of the electrode used for stimulation (e.g., size, shape, surface area, intervening tissue impedance, etc). Representative stimulus parameters can include: (a) a pulse magnitude of about 1 microamp to about 100 milliamps; (b) a pulse period of about 0.01 milliseconds to about 100 milliseconds; (c) a pulse frequency of about 0.1 pulses per second to about 1000 pulses per second; and (d) a duty cycle of about 1% to about 100%.

A representative stimulation used in the methods of the present invention can further comprise biphasic stimulation, wherein the cathodal phase and anodal phase of each pulse are adjusted to deliver a preferred net charge to tissue over time. When a biphasic stimulation is employed, the duration of the cathodal phase, the duration of anodal phase, or the duration of each the cathodal and anodal phases is optionally increased to about 100 milliseconds or more.

In another embodiment of the invention, an effective amount of stimulation comprises an amount equal to or greater than a threshold amount, wherein the threshold amount of stimulation can be administered at any convenient frequency. A threshold amount can be expressed, for example, as a number of stimulus pulses administered, wherein each pulse has a specified magnitude. At a selected frequency, the number of pulses can be determined by multiplying the frequency by the duration of the stimulus interval.

In still another embodiment of the invention, the stimulating comprises providing an effective amount of a pharmacological agent. Thus, the present invention further provides that a small molecule or a protein encoded by a gene therapy vector could modulate gene expression in a manner similar to that elicited by electrical or magnetic stimulation. For example, a small molecule could be used to express genes that control receptivity of a target tissue to reinnervating neurons.

In accordance with the methods of the present invention, stimulation of a muscle to promote selective reinnervation might also produce muscle twitching and/or tetanization. However, an effective amount of stimulation does not necessarily comprise an amount of stimulation to elicit tetanization and muscle movement. Thus, in contrast to existing methods that employ muscle stimulation to artificially produce muscle contraction and movement, the present invention provides a method for stimulating the muscle to promote selective reinnervation.

An effective amount of stimulation can comprise a range of stimulus types and amounts. Representative methods for determining an effective amount of stimulation in a model system are described in Example 2. One skilled in the art can readily assess the efficacy of promoting muscle reinnervation and adjust the therapeutic regimen accordingly, upon review of the disclosure of the invention presented herein.

The present invention further provides that stimulating a denervated target tissue is preferably performed as soon as possible following injury or disease resulting in denervation. Existing practices that are directed at stimulating a muscle to produce contraction typically include an extended period (e.g., 6 months) following denervation and prior to stimulation to permit spontaneous reinnervation to occur. See e.g., U.S. Pat. No. 5,897,579. In particular, stimulation during this period is thought to interfere with possible recovery via spontaneous reinnervation. In contrast, the present invention provides methods for enhancing selective reinnervation and functional recovery via stimulation of the target tissue shortly following denervation.

III.A. Laryngeal Paralysis

In a preferred embodiment of the present invention, a denervated muscle is stimulated to promote reinnervation of the muscle. More preferably, the methods of the present invention can be used to stimulate laryngeal muscles to promote reinnervation of nerve fibers in the RL nerve or superior laryngeal nerve.

Laryngeal paralysis is a debilitating clinical problem. When the nerves innervating the laryngeal muscles are injured on both sides, the patient can no longer open (abduct) the glottal vocal folds during breathing. A tracheotomy can be performed emergently followed by a partial resection of the vocal fold in case of prolonged paralysis to restore ventilation through the mouth. However, the procedure sacrifices the voice and compromises the ability to swallow without aspiration. A more physiological approach to treatment involves functional electrical stimulation of the vocal fold abductor (PCA) muscle in pace with inspiration (Zealear & Dedo, 1977).

The present invention provides methods for restoring vocal fold motion via selective reinnervation, as described in Example 1. Using this approach, the PCA muscles are stimulated, whereby reinnervation by inspiratory motoneurons is enhanced and reinnervation by foreign motoneurons is inhibited.

Figure 1B:
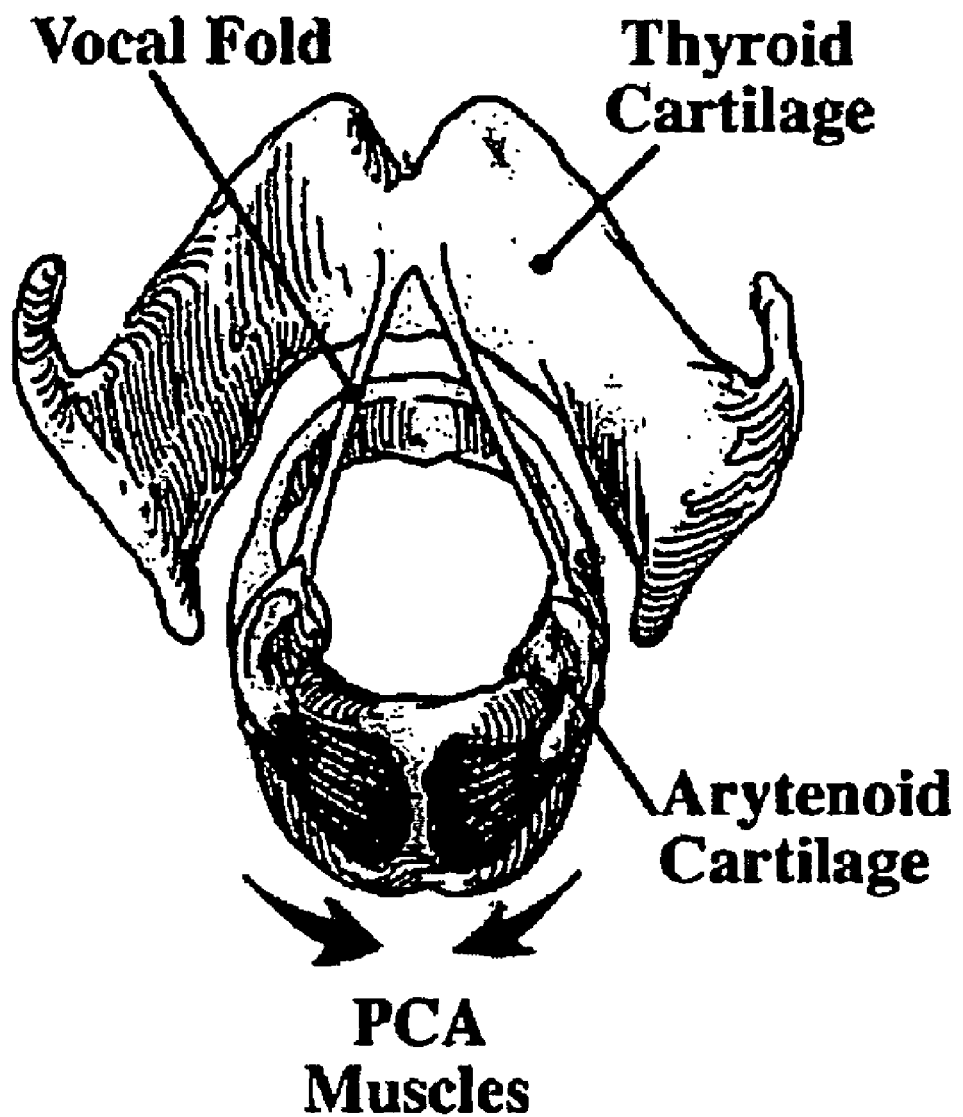
Figure 1C:
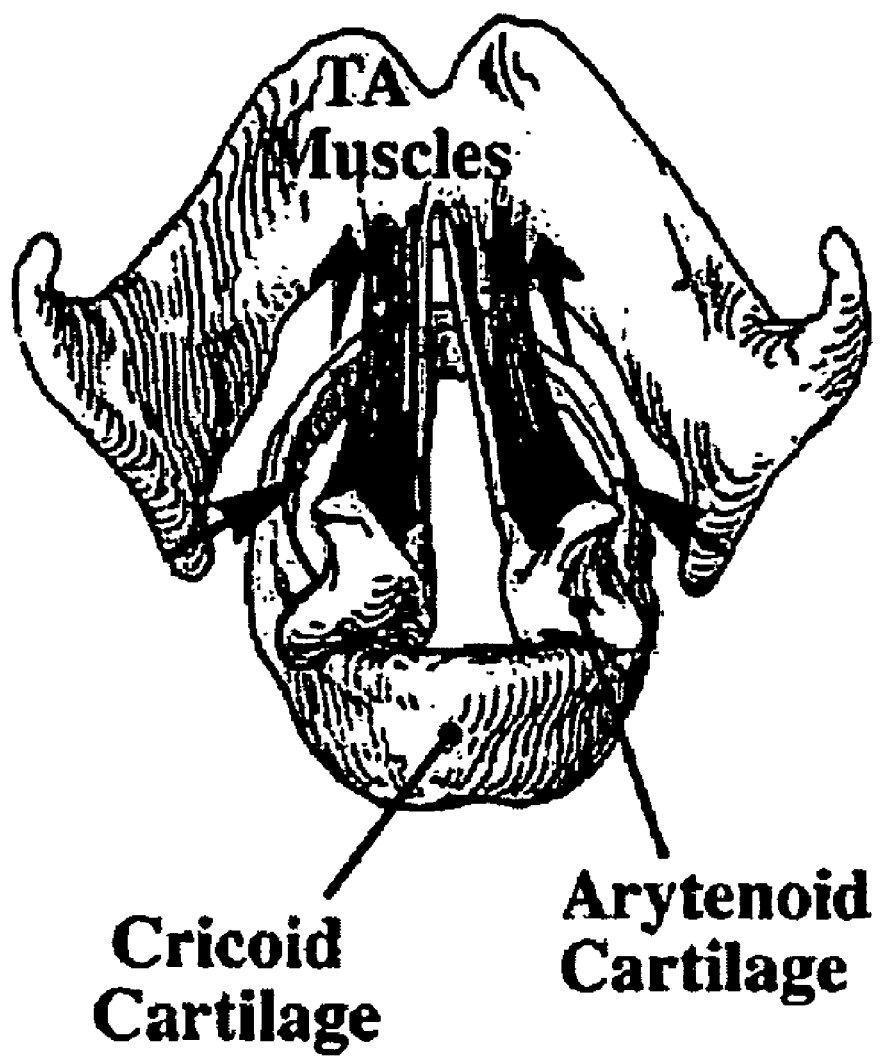

As a matter of orientation, the paired PCA abductor muscles are situated on the posterior larynx (FIG. 1A). When the PCA contracts, it rocks the arytenoid cartilage in a posteromedial direction to open the vocal fold (FIG. 1B). The thyroarytenoid (TA) muscle is the principal adductor of the vocal folds to close the glottic airway (FIG. 1C). Both abductor and adductor muscles are supplied by motor fibers in the RL nerve. Injury to the RL nerve commonly results in misdirected regeneration to the PCA muscle and its antagonists, resulting in a functionally paralyzed but synkinetically reinnervated larynx.

The abductor and adductor muscles are distinguished with respect to their motor unit composition. The PCA muscle exclusively contains inspiratory motor units that increase firing during hypercapneic or hypoxic conditions (Insalaco et al., 1990). In contrast, the TA muscle and its synergists exclusively contain reflex glottic closure (RGC) motor units that close the glottis reflexly on activation of sensory receptors within the laryngeal mucosa. The internal branch of the superior laryngeal nerve is a purely sensory nerve containing the afferent fibers of these receptors (Ludlow et al., 1992).

Example 1 demonstrates that chronic electrical stimulation of the PCA muscle promotes selective reinnervation of native over foreign motoneurons. All of the stimulated experimental animals showed significantly greater appropriate reinnervation and less inappropriate reinnervation than nonstimulated control animals. Although significance was not demonstrated, electrical stimulation apparently increased the overall magnitude of reinnervation, presumably due to the protective effect of stimulation in preventing muscle atrophy.

Preservation of the viability of muscle fibers and endplates could enhance overall reinnervation irrespective of motoneuron type. However, this protective effect cannot explain the observed change in preference of the stimulated PCA muscle for native over foreign motoneurons. Animals in the experimental group that had a greater level of correct reinnervation also had a lower level of incorrect reinnervation. In contrast, control animals did not show such a reciprocal relationship. In fact, just the opposite was observed: a greater level of correct reinnervation was paralleled by a greater level of incorrect reinnervation. These observations suggest that chronic stimulation induced a bias in endplate affinity for competing motoneurons, in which the original motoneuron was favored.

III.B. Stimulator Devices

In accordance with the methods of the present invention, a target tissue can be stimulated using a stimulator device. A stimulator can comprise one or more signals generators. When a plurality of signal generators is used, each of the plurality of generators can produce a same or different signal. Preferably, a stimulator device is programmable such that the stimulation can be delivered in a controlled manner.

A device for providing stimulation can be variably constructed for suitability to an intended site of stimulation. Thus, a stimulator device can comprise any appropriate size and shape such that the device can provide stimulation to a denervated target tissue. Further, the stimulator device can be constructed of any material compatible with its intended placement and can further comprise an electrically insulative coating. Design or selection of a stimulator device can be accomplished by one of skill in the art.

In one embodiment of the invention, a stimulator device is constructed for exterior placement and stimulation of an underlying muscle in need of treatment. Thus, a stimulator device can comprise a garment or other material adapted for external placement on a subject, for example as described in U.S. Pat. Nos. 6,233,472; 6,226,552; 6,217,491; and 5,562,707.

In another embodiment of the invention, a stimulator device comprises an injectable or implantable stimulator. A stimulator that is placed in vivo can optionally be controlled noninvasively, for example via a radio frequency transmitter located outside the body. Representative injectable or implantable devices for electrical stimulation are disclosed in U.S. Pat. Nos. 6,243,607; 6,163,725; 6,134,469; 6,051,017; 5,991,649; and 5,366,493.

As described herein below, a preferred embodiment of the invention comprises stimulating a denervated laryngeal muscle. The ITREL II® stimulator (Medtronic of Minneapolis, Minn., United States of America) is suitable for electrical stimulation of laryngeal muscles as described by Billante et al. (2002) Ann Otol Rhinol Laryngol 111:328-332 and by Zealear et al. (2002) Ann 0 to 1 Rhinol Laryngol 111:500-506.

Additional representative devices for electrical stimulation are disclosed in U.S. Pat. Nos. 6,132,387; 6,029,090; 5,983,140; 5,690,692; and 5,571,148.

Representative devices for magnetic stimulation are disclosed in U.S. Pat. Nos. 6,179,771; 6,123,658; and 6,132,361.

III.C. Molecular Components of Reinnervation

Target tissue stimulation could induce gene expression in the tissue that encourages reinnervation by appropriate motoneurons, promotes the selective pruning of inappropriate reinnervation, or a combination thereof. To identify these genes, the mRNA profiles of a stimulated target tissue can be compared to that of unstimulated target tissue, for example by microarray technology as described in Example 4. The gene products identified can be used to develop pharmacological therapies for appropriate reinnervation of muscle denervated by disease or injury.

Thus, the present invention also encompasses stimulating a denervated target tissue via altering gene expression in the target tissue. The phrase "altering gene expression" generally refers to eliciting a change in RNA or protein levels, including an increase or decrease of particular RNAs and proteins. Altered gene expression in the target tissue could, for example, modulate molecular processes of reinnervation, such as recognizing, attracting, or securing native neurons and/or repelling or pruning foreign neurons.

III.D. Assessment of Reinnervation

The quality and magnitude of reinnervation can be evaluated to assess the effectiveness of target tissue stimulation treatment. Preferably, performance of a disclosed method promotes an increased magnitude of reinnervation, an improved quality of reinnervation, or a combination thereof.

The phrase "magnitude of reinnervation" as used herein refers to a quantity of re-established neuronal connections.

The phrase "quality of reinnervation" as used herein refers to the extent of correct reinnervation versus incorrect reinnervation. The quality of reinnervation can be expressed quantitatively as the reinnervation quality index (RQI), which is a ratio of correct reinnervation relative to incorrect reinnervation as described in Example 1. An improved quality of reinnervation is characterized by an increased amount of correct reinnervation and a lesser amount of incorrect reinnervation.

Reinnervation can be assessed using a variety of electrophysiological techniques known to one of skill in the art including electromyography, reflexmyography, and magnetic stimulated myography. See Example 1 and Pototschnig & Thumfart (1997) Acta Otorhinolaryngol Belg 51(2):99-104. In one embodiment of the invention, a device for monitoring electrophysiological activity is a same device for providing stimulation. A representative stimulus generator/monitor is described in U.S. Pat. No. 5,480,416.

The appropriateness of neuronal projections can also be determined by: (a) detection of a neurotransmitter within the target tissue, for example as described in U.S. Pat. No. 5,721,243; (b) labeling reinnervating neurons with fluorescent tracers, for example as described in Example 3; and (c) assessing functional recovery of the target tissue in performing relevant tasks.

III.E. Combined Therapies for Nerve Regeneration and Selective Reinnervation

The method for promoting selective reinnervation as disclosed herein can further be combined with therapies for promoting nerve regeneration. For example, in one embodiment, muscle stimulation to promote muscle reinnervation is performed prior to, coincident with, or following a provision of a therapeutic composition that induces or supports neuronal growth. Representative compositions can include neurotrophic factors, cytokines, or extracellular matrix molecules. See e.g., Di Giulio et al. (2000) Int J Dev Neurosci 18(4-5):339-346 and U.S. Pat. Nos. 5,898,066 and 5,504,197. Similarly, the disclosed methods can be used in conjunction with prostheses, such as channels, conduits, or cellular scaffolds, which mediate and direct nerve growth. See e.g., Evans (2000) Semin Surg Oncol 19(3):312-318; Hall (1997) J Anat 190(Pt 1):57-71; and U.S. Pat. Nos. 6,365,149 and 6,214,021.

III.F. Subjects

With respect to the therapeutic methods of the present invention, a preferred subject is a vertebrate subject. A preferred vertebrate is warm-blooded; a preferred warm-blooded vertebrate is a mammal. A preferred mammal is a mouse or, most preferably, a human. As used herein and in the claims, the term 'subject' includes both human and animal subjects. Thus, veterinary therapeutic uses are provided in accordance with the present invention.

Also provided is the treatment of mammals such as humans, as well as those mammals of importance due to being endangered, such as Siberian tigers; of economical importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, provided is the treatment of livestock, including, but not limited to, domesticated swine, ruminants, ungulates, horses (including race horses), poultry, and the like.

EXAMPLES

The following Examples are included to illustrate modes of the invention. Certain aspects of the following Examples are described in terms of techniques and procedures found or contemplated by the present inventor to work well in the practice of the invention. The Examples illustrate standard laboratory practices of the inventor. In light of the present disclosure and the general level of skill in the art, those of skill will appreciate that the following Examples are intended to be exemplary only and that numerous changes, modifications and alterations can be employed without departing from the scope of the invention.

Example 1

Electrical Stimulation of a Denervated Muscle Promotes Selective Reinnervation

The effect of electrical stimulation of the denervated posterior cricoarytenoid (PCA) muscle on its subsequent reinnervation was explored in the canine. Eight animals were implanted with planar electrode arrays for chronic stimulation and EMG recording across this fan-shaped muscle surface. Four animals were continuously stimulated for the duration of the 11-month experiment; the remaining four served as nonstimulated controls. Quantitative techniques were developed to determine the extent of appropriate reinnervation by intrinsic motoneurons and inappropriate reinnervation by antagonist motoneurons. All four experimental animals showed a greater level of correct and a lesser level of incorrect reinnervation than the controls, on both electromyographic and behavioral grounds. Thus, electrical stimulation improved the quality of muscle reconnection by suppressing incorrect and enhancing correct reinnervation. Stimulation also enhanced the overall magnitude of reinnervation but this effect was less robust.

Methods

Surgery and Assessment of Implant Stability. Animal care was conducted in accordance with the National Institutes of Health Guide for the Care and Use of Laboratory Animals. Under isofluorane gas anesthesia, a patch electrode array was implanted in each of 10 canines, each animal weighing 20-25 kg.

The patch was configured in a 6×6 matrix of electrodes to allow discrete stimulation and EMG recording at any site on either PCA muscle. Each TEFLON®-coated (E.I. du Pont De Nemours and Company of Wilmington, Del., United States of America) stainless steel lead wire was deinsulated 1.5 mm at the tip. The circuit included small outline integrated circuit components. Nerve stimulus cuffs were optionally included in the implant design. A receptacle containing wire terminations from the patch was tunneled subcutaneously to the skull and anchored with bone cement. A pacing circuit was encased in a box with an interface plug constructed complementary to the skull receptacle. See Zealear et al. (2002) *J Neurophysiol* 87:2195-2199.

Following implantation, each animal was examined every 3 to 4 weeks to assess implant stability. The animal was anesthetized with 10 mg/kg pentobarbital sodium and maintained in a moderate plane of anesthesia in a supine position. A zero degree endoscope (Henke Sass Wolfe model available from Ashtead Technologies of Rochester, N.Y.) was inserted through a laryngoscope to videomonitor and measure spontaneous or stimulated vocal fold motion. The magnitude of abduction from the glottal midline was measured on a superimposed grid, calibrated by a ruler placed on the vocal fold.

The positional stability of the patch electrode array was assessed by stimulating sequentially at each of its 36 electrode sites while monitoring the magnitude of evoked abduction, producing a "map" of the most effective stimulation sites on the PCA muscle. Normative evoked EMG (EEMG) recordings were obtained at each of these sites elicited by supramaximal stimulation of the RL nerve with a percutaneous needle electrode. Eight of the 10 animals demonstrated implant stability with stimulation and recording during a period of four months, and these animals were randomized into experimental or control groups. Experimental and control animals were thereafter treated blindly, i.e., without knowledge of the animal's group assignment. Each animal was assigned a number identity, which corresponded to its position in the implant sequence.

During a second operative procedure, the right RL nerve was sectioned and reanastomosed 5-6 cm from the larynx in each animal. A pacemaker circuit was attached to the skull receptacle of the experimental animals (animals *2, *3, *6, and *7 in Table 1). A 1-second, biphasic, charge-balanced pulse train with a frequency of 30 pps, pulse width of 1 msec, and amplitude of 2-6 mA was delivered at four PCA muscle sites to produce a moderate level of abduction on the paralyzed side (2-4 mm). This stimulus paradigm was repeated every 10 seconds and was applied continuously for the entire 11-month study. Nonstimulated animals (animals 1, 4, 5, and 8 in Table 1) served as controls. After RL nerve section and repair, each animal rotated through the laboratory for a monthly physiological session.

Physiological Sessions. All physiological sessions were conducted under TELAZOL® anesthesia (Parke, Davis and Co. of Detroit, Mich., United States of America) delivered intravenously at a rate of 1.4 mg per kg per hour to maintain laryngeal reflexes and respiratory response to inhaled $CO_2$.

Figure 2A:
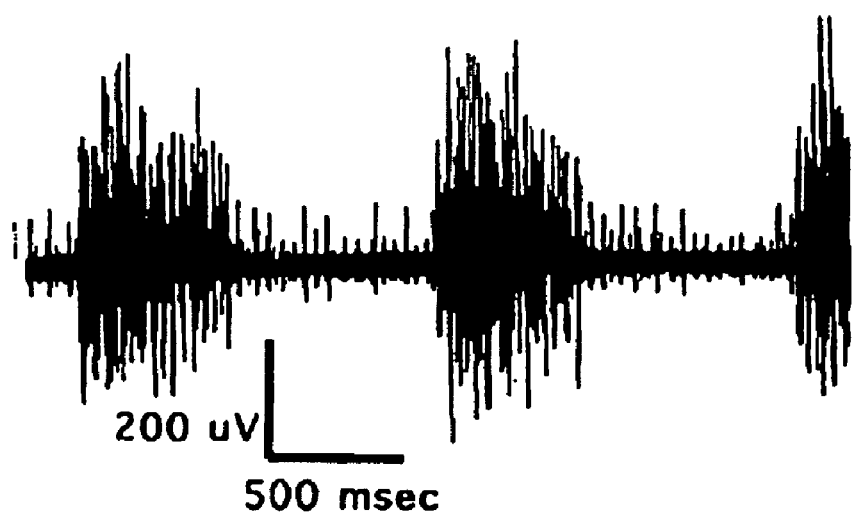
FIGS. 2A-2D are recordings from a same PCA muscle electrode site during different activities. The latency following inadvertent vagus nerve stimulation (FIG. 2C) is increased when compared with the latency following RL nerve stimulation (FIG. 2B) due to an increased conduction path. The latency is further increased when RGC motor units are activated polysynaptically via superior laryngeal nerve stimulation (FIG. 2B). The response due to direct activation of PCA motor fibers (FIG. 2C) can be distinguished from an indirect response (FIG. 2D) based on the latency and waveform differences as illustrated.

Appropriate PCA muscle reinnervation was measured in two ways. First, the change in cross-sectional area of the (glottal) airway with spontaneous vocal fold abduction was measured. Specifically, two video still frames representing the vocal folds at rest and maximally abducted were digitized and analyzed using computer morphometry (ADOBE PHOTOSHOP® computer program by Adobe Systems Inc. of San Jose, Calif., United States of America). A line was drawn from the anterior commissure to the posterior commissure of each frame to allow independent measurement of the hemiglottal area on each side. The percent change in hemiglottal area was determined by the change in number of pixels. Four trials were run during normal breathing or hypercapneic conditions. Second, the magnitude of appropriate PCA muscle reinnervation was based on direct recordings of spontaneous EMG activity when respiratory drive was maximized by administration of $CO_2$ mixed with room air. Exposure was limited to 1-2 minutes during which time maximum inspiratory motor unit recruitment occurred (FIG. 2A). Recordings at an electrode site were amplified, rectified, and integrated over an 8-second time interval. The mean value obtained at all muscle sites was averaged to give an overall index of its inspiratory capacity.

To quantify the level of aberrant PCA muscle reinnervation by RGC motoneurons, two different approaches were taken to activate these motor units via sensory stimulation. In the first approach, sensory nerve fibers within the vocal fold mucosa were electrically stimulated using a sponge electrode saturated with saline. In the second approach, the internal branch of the superior laryngeal nerve was stimulated with a percutaneous needle electrode. Sensory-elicited motor unit activity was recorded across the PCA muscle at the same electrode sites used previously for quantifying inspiratory activity (e.g., FIG. 2D). RGC unit activity recorded at a site was quantified by rectification and integration over a 20-millisecond window, which was positioned in time to capture the entire RGC waveform. The average across all sites gave an estimate of the incorrect reinnervation of the muscle.

Figure 2B:
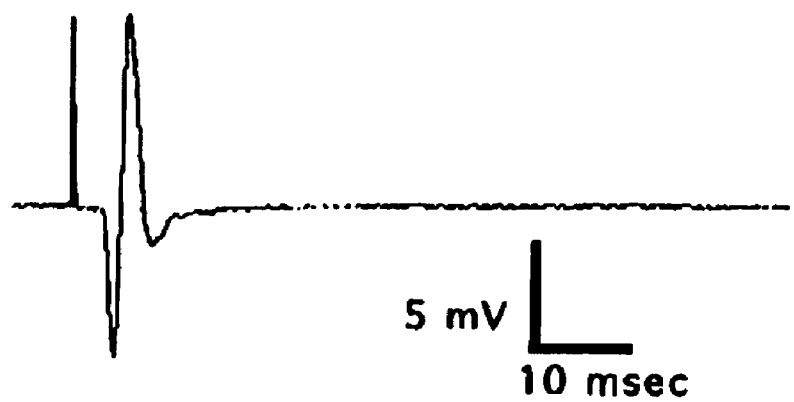
Figure 2C:
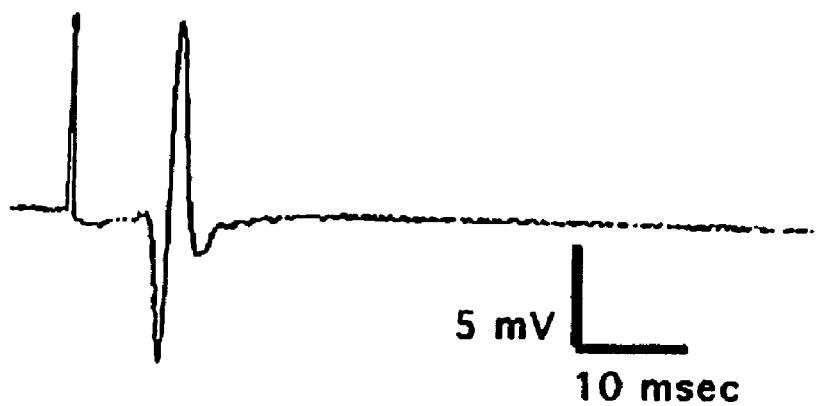
Figure 2D:
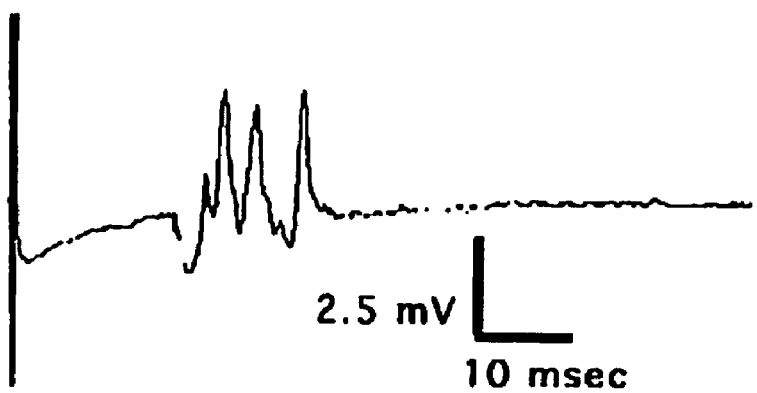

The magnitude of PCA reinnervation was measured in each session. EEMG responses were recorded sequentially at each muscle site following RL nerve stimulation proximal to the anastomosis (FIG. 2B). The average EEMG response recorded from all sites across the surface of the PCA muscle gave a good index of the overall magnitude of its reinnervation. EEMG motor unit activity was rectified and integrated over a 10-millisecond window.

Statistical and Data Analysis. A two-tailed, unpaired Student's t-test was used to assess differences in stimulated and nonstimulated animals. The following parameters were used to assess reinnervation and PCA muscle performance: percent change in hemiglottal area, inspiratory unit amplitude, RGC unit amplitude, and EEMG amplitude. In stimulated (experimental) animals, the indicated outcomes were determined for the denervated and stimulated muscle. In nonstimulated (control) animals, the indicated outcomes were determined for the denervated and nonstimulated muscle. The performance of the nondenervated PCA muscle was also assessed in each stimulated animal and nonstimulated animal, and these values were used to normalize the data presented in Table 2.

The calculations presented in Tables 1 and 2 are derived from the same raw data using different analytical approaches, as described further herein below. Briefly, Table 1 is an initial compilation of data from individual experiments that assess PCA muscle performance following denervation. Table 2 summarizes PCA muscle performance following denervation relative to the performance of a nondenervated muscle. Thus, Table 2 reflects a more comprehensive analysis and is therefore referenced in the following discussion of results.

In Table 1, the values shown in parentheses represent measurements of the indicated parameter, in which each raw value is expressed as a percentage of the maximum raw value observed on the denervated side of any animal. Based on this normalization, the PCA performance for each animal and a given parameter were ranked according to the percentile values. Glottal opening (GA) measurements are shown for each of four trials.

The values in parentheses presented in Table 2 also represent measurements taken on the denervated side of each animal. In this case, the raw data measurements were normalized to the average value obtained for that parameter on the nondenervated side. Thus, the percentile rating of reinnervated PCA muscle performance was referenced to that of the average normally innervated muscle. The average value in glottal opening ($\Delta GA$) was determined based on the individual measurements of glottal opening (GA) in each of four trials displayed in Table 1. The rank order of PCA performance for each parameter is identical in Table 1 and Table 2, despite the differences in percentile rating introduced by using two different calculation methods.

Results

Quality of Reinnervation. The quality of PCA reinnervation was determined in each animal by establishing the relative level of correct and incorrect muscle reconnection. The extent of appropriate reinnervation was determined by measuring inspiratory-related activity of the PCA, while the level of inappropriate reinnervation was determined by measuring PCA activity that was elicited by sensory stimulation. This latter type of activity is normally mediated by antagonist adductor muscle motor units for reflex glottic closure (RGC). These motor units are not present in the normally innervated abductor PCA muscle. The presence of RGC motor units in the antagonist, TA (thyroaytenoid), muscle and absence of RGC motor units in the PCA on the normally innervated side was confirmed in each animal.

Appropriate Reinnervation by Native Motoneurons. The level of correct (inspiratory) PCA activity was measured in two ways. First, the magnitude of spontaneous vocal fold abduction produced with PCA contraction was measured during inspiration. The percent change in hemiglottal area was measured independently by two investigators from video still frames using computer morphometry.

Two series of sessions (GA1 and GA2) were run on animals in light plane of anesthesia to estimate the change in hemiglottal area. Although results from the two series were consistent, it was believed that animals might have differed in the respiratory drive of the PCA. Therefore, a third and fourth series (GA3 and GA4) were run under hypercapneic conditions in which animals were induced to maximally respirate through inhalation of $CO_2$ mixed with room air. Exposure to $CO_2$ was limited to 1-2 minutes during which time maximum abduction was observed in each animal. In the fourth series, a short-acting neuromuscular blocking agent (pancuronium bromide) was also injected into the antagonist TA muscle so that glottal opening would reflect inspiratory activity of the PCA in the absence of competitive synkinetic inspiratory activity in the TA. For GA3 and GA4, the relative performance of the animals was identical in the presence or absence of TA muscle blockade. Each animal's performance was given a numerical rank, with "1" indicating the best performance and "8" indicating the worst performance, as shown in Table 2.

The spontaneous vocal fold abductions observed were strikingly different among animals irrespective of test conditions. Animals *2 and *6 showed near-normal recovery of vocal fold motion in stimulated animals when compared to nonstimulated animals. In contrast, control animals 4, 8, and 5 exhibited spontaneous adductory motion on the reinnervated side with net loss in glottal area during inspiration. Animals *7, *3, and 1 showed intermediate levels of abduction.

The second method of estimating inspiratory capacity of the PCA muscle was based on direct recordings of spontaneous EMG activity when respiratory drive was increased by $CO_2$/air administration. Exposure was limited to 1-2 minutes during which time maximum inspiratory unit recruitment occurred. Recordings at an electrode site were rectified and integrated over a specified time interval. The mean value obtained at sites, which spanned the entire PCA, were averaged to give an overall index of PCA inspiratory capacity. As shown in Table 2, the ranked order of animals was nearly identical to that observed for the average GA series.

Possibly the best estimate of PCA inspiratory capacity would reflect both the electrical activity of the muscle (inspiratory EMG) and the mechanical activity produced by its contraction ($\Delta GA$). Using normalized values for each series, the overall mean of percentile ratings across the four series was calculated for each animal, and then averaged with the percentile rating obtained for inspiratory EMG performance. The results are shown in Table 2, column 3. All of the experimental animals ranked higher than the control animals, and there was a significant gap between *3 and 1, the worst experimental animal and best control animal. These data demonstrate that chronic electrical stimulation enhanced correct reinnervation of the PCA muscle ($P<0.0064$).

Inappropriate Reinnervation by Foreign Motoneurons. The greater level of correct PCA reinnervation in the experimental animals could reflect a greater magnitude of overall reinnervation of the PCA. Stated another way, incorrect reinnervation by reflex glottic closure motoneurons could have also been enhanced by chronic pacing.

To quantify the level of aberrant reinnervation of the PCA by RGC units, two different approaches were taken two activate these motor units via sensory stimulation, as described herein above. Similar results were obtained with either approach, however, superior laryngeal nerve stimulation was believed to be more reliable. Activation of the entire internal branch of the nerve insured maximum and consistent recruitment of RGC motor units in each of separate trials. The rank and percentile ratings of each animal with respect to level of RGC activity with SLN stimulation are shown in Table 2, column 4. All experimental animals demonstrated lower levels of RGC activity and ranked higher than control animals. These data demonstrate that chronic electrical stimulation suppressed incorrect reinnervation of the PCA muscle ($P<0.0084$).

Magnitude of Reinnervation. To determine the magnitude of PCA reinnervation, evoked electromyography (EEMG) responses were recorded sequentially at each muscle site following stimulation of the RLN. The average EEMG response recorded from all sites across the surface of the PCA gave a good index of the overall magnitude of reinnervation of a muscle.

Changes in percent reinnervation of a muscle relative to its initial (innervated) state were determined by normalizing the average EEMG recording from each session to that obtained before nerve section. Ratios steadily increased during the first 5 months and then plateaued over the remaining 6 months of investigation. The latter asymptomatic stage signaled the completion of the reinnervation process during which the outcome parameter values were obtained. The rank order and percentile ratings for EEMG are shown in Table 2, column 5.

A second approach used to estimate the magnitude of PCA reinnervation simply summed the levels of correct and incorrect reinnervation, and expressing the sum as a percent of a similar sum of values obtained for the normal (nondenervated) side. For example, in Table 2, correct reinnervation is listed in column 3, incorrect reinnervation is listed in column 4, and the sum value expressed as a percent of the sum on the normal side is listed in column 6.

There was general agreement in the ranking of animals with respect to reinnervation magnitude using the above-mentioned methods, with the exception of animal *7 and animal 1. An additional rank and percentile rating of each animal was calculated by averaging the data obtained by each method, as shown in Table 2, column 7. Regardless of the method of assessment, the four experimental animals were in the top six of the rank list and experienced a greater level of reinnervation than the control animals. Chronic pacing appeared to increase the overall magnitude of PCA reinnervation, however, this increase was not statistically significant ($P<0.113$).

SUMMARY

In comparing columns 3 and 4 of Table 2, an experimental animal that had a greater level of correct reinnervation also had a lower level of incorrect reinnervation; the order of ranking for correct and incorrect was identical except for the switch between animals *7 and *6. Control animals did not show such a reciprocal relationship. In fact, just the opposite was observed. The greater the level of correct reinnervation for a control animal, the greater the level of incorrect reinnervation (i.e. the rank order for correct "1, 4, 8, 5" was reversed for incorrect "5, 8, 4, 1").

Chronic electrical stimulation also enhanced the overall level of reinnervation in a subset of the animals, as shown in Table 2, column 7. Two of the control animals (1, 4) experienced a greater overall level of reinnervation than one of the experimental animals (*3).

Since the quality of reinnervation of a muscle is related to the level of correct and inversely related to the level of incorrect reinnervation, the overall quality was further estimated by the ratio of correct (C) to incorrect (I). The ratio has been termed the reinnervation quality index (RQI) for the purpose of this Example. The rank order of RQI values for the animals is shown in column 8. All of the experimental animals showed greater appropriate reinnervation and less inappropriate reinnervation when compared to control animals. Thus, chronic electrical stimulation of the PCA muscle promoted selective reinnervation by native motoneurons over foreign motoneurons.

TABLE 1

| Animal Rank | Correct Reinnervation Trials | | | | | Av. Correct Rein. (C) | Av. Incorrect Rein. (I) | | Reinnervation Magnitude | | |
|---|---|---|---|---|---|---|---|---|---|---|---|
| | 1 GA1 | 2 GA2 | 3 GA3 | 4 GA4 | 5 Insp EMG | 6 GAs + Insp EMG Av. | 7 SLN stim EMG | C/I 8 RQI | 9 C + I Activity | 10 Patch EEMG | 11 Av. C + I + EEMG |
| Normal | NA | 86% | 66% | 91% | 110% | 96% ± 20 | 13% ± 5 | 7.5 | 87% | 106% ± 3 | 102% |
| 1 | *2 | *6 | *2 | *2 | *2 | *2(100 ± 4) | *2(26 ± 2) | *2(3.9) | 1(100) | *7(100 ± 0) | *2(100) |
| 2 | *6 | *2 | | | | *6(83 ± 21) | *7(36 ± 6) | *6(2.2) | *2(96) | *2(93 ± 5) | *6(94) |
| 3 | *3 | 4 | *7 | *7 | *7 | *7(54 ± 0.4) | *6(37 ± 9) | *7(1.5) | *6(92) | *6(85 ± 2) | 1(93) |
| 4 | 1 | *3 | *3 | *3 | *3 | *3(52 ± 1) | *3(45 ± 4) | *3(1.1) | 4(75) | 1(75 ± 3) | *7(90) |
| 5 | *7 | 1 | 1 | 1 | 4 | 1(31 ± 14) | 5(55 ± 3) | 1(0.3) | *3(74) | *3(70 ± 2) | 4(80) |
| 6 | 4 | *7 | 8 | 8 | 1 | 4(18 ± 12) | 8(69 ± 8) | 4(0.23) | *7(69) | | *3(77) |
| 7 | 8 | 8 | 4 | 4 | 8 | 8(9 ± 9) | 4(79 ± 11) | 8(0.15) | 8(60) | 5(68 ± 4) | 8(63) |
| 8 | 5 | 5 | 5 | 5 | 5 | 5(0 ± 0) | 1(100 ± 5) | 5(0.0) | 5(42) | 8(58 ± 4) | 5(59) |

Av. = average
C = correct reinnervation
EEMG = evoked electromyography
EMG = electromyography
GA = hemiglottal area
I = incorrect reinnervation
Insp = inspiratory
RQI = Reinnervation Quality Index
SLN = superior laryngeal nerve
stim = stimulation

TABLE 2

| Animal Rank | Correct Reinnervation Trials | | Average Correct Reinnervation 3 | Average Incorrect Reinnervation | Magnitude Reinnervation Trials | | Average Magnitude Reinnervation 7 | RQI |
| --- | --- | --- | --- | --- | --- | --- | --- | --- |
| | 1 ΔGA | 2 Inspiratory EMG | Inspiratory EMG + ΔGA Average | 4 SL nerve stimulation EMG | 5 Patch EEMG | 6 C + I Activity | EEMG + (C + I) Average | 8 C/I |
| Normal | N(100% ± 8) = 43% ΔGA | N(100 ± 11) = 223 μV-s | N(100) | N(12.7 ± 5) = 68.8 μV-s | N(100 ± 2) = 1,750 μV-s | N(100) | N(100) | N(7.87) |
| 1 | *2(114 ± 10) | *2(91 ± 0.5) | *2(102 ± 11) | *2(26 ± 1) | *7(94 ± 0.2) | 1(114) | *2(100.4 ± 13) | *2(3.92) |
| 2 | *6(99 ± 24) | | *6(99) | *7(36 ± 6) | *2(87 ± 3) | *2(113) | *6(100.3 ± 20) | *6(2.68) |
| 3 | *7(64 ± 12) | *7(47 ± 0.9) | *7(56 ± 9) | *6(37 ± 9) | *6(80 ± 2) | *6(120) | 1(93 ± 22) | *7(1.56) |
| 4 | *3(62 ± 6) | *3(44 ± 1.1) | *3(53 ± 9) | *3(45 ± 4) | 1(71 ± 2) | 4(93) | *7(88 ± 6) | *3(1.18) |
| 5 | 1(52 ± 5) | 4(15 ± 1.3) | 1(29 ± 24) | 5(55 ± 3) | 4(70 ± 9) | *3(87) | 4(82 ± 11) | 1(0.29) |
| 6 | 4(36 ± 13) | 1(5 ± 1.1) | 4(25 ± 11) | 8(69 ± 8) | *3(66 ± 1) | *7(82) | *3(77 ± 10) | 4(0.32) |
| 7 | 8(22 ± 10) | 8(0.3 ± 0.1) | 8(11 ± 11) | 4(79 ± 11) | 5(64 ± 2) | 8(71) | 8(63 ± 8) | 8(0.16) |
| 8 | 5(0 ± 0) | 5(0 ± 0) | 5(0 ± 0) | 1(100 ± 5) | 8(55 ± 3) = 955 μV-s | 5(49) | 5(56 ± 8) | 5(0.00) |

C = average correct reinnervation
EEMG = evoked electromyography
EMG = electromyography
ΔGA = average change in hemiglottal area
I = average incorrect reinnervation
N = normal value
RQI = Reinnervation Quality Index
SL = superior laryngeal In each entry of Table 2, the reinnervated PCA muscle of each animal is identified by its number (e.g., 1, *2, *3, 4, 5, *6, *7, or 8) followed by its percentile ranking in parentheses. Reinnervated muscles in the experimental stimulated group are distinguished by asterisks (*2, *3, *6, and *7). Reinnervated muscles in the control group are not marked with asterisks (1, 4, 5, and 8). The average normally innervated muscle is identified by "N." Raw data for outcome parameters are shown for average innervated PCA muscle and the worst ranked reinnervated PCA muscle. SL nerve, internal branch of superior laryngeal nerve. Animal *6 correct reinnervation ranking was determined using the average of ΔGA1 and ΔGA2 performance.

A ranking of animals based on the extent of incorrect reinnervation was determined by mucosal sponge stimulation. For animal *6, a value of 81% was derived for inspiratory EMG through interpolation of column 1 with column 2 data. If the interpolated value is used, it only changes the rank of animal *6 with respect to (C+I) activity (Column 6): rank decreases from first to third, and percentile rating decreases from 120% to 112%. Animal 4 correct reinnervation and incorrect reinnervation rankings were determined by averaged recordings across 12 representative patch sites using invasive electrodes.

Example 2

Stimulus Paradigms

Eighteen canines are enrolled in a study of patterned electrical stimulation. An additional three animals serve as non-stimulated controls. The PCAs of nine animals are stimulated with a tonic activity pattern at 20 pulses/second, and the remaining nine are stimulated with a phasic pattern at 100 pulses/second. Since another key feature that appears to control muscle contractile properties is the amount of activity associated with tonic and phasic firing, the tonic and phasic groups are further subdivided into three groups exposed to different activity amounts (e.g., 60, 300, and 600 pulses every minute). The activity amount can be varied by changing the duration of the pulse train. Stimulus pulse trains are repeated every ten seconds and applied during a period of about four months. Animals are treated and evaluated as described in Example 1, with the exception that stimulation parameters are varied as just described.

Example 3

Retrograde Tracer Study to Identify Reinnervating Motoneurons

A first tracer (e.g., fast blue) is injected into the PCA during implant surgery to label the original PCA motoneurons. In the terminal session, the PCA is injected with a second tracer (e.g., nuclear yellow) to label the reinnervating motoneurons. Labeled neurons are visualized by fluorescence microscopy.

Example 4

Microarray Analysis of FES-Induced Gene Expression

Gene expression is compared in stimulated and nonstimulated animals at multiple time points following unilateral denervation. The denervated PCA muscle is stimulated using a pattern determined to be efficacious at promoting appropriate reinnervation. Useful time points include: (a) before the onset of reinnervation onset (e.g., day 0 through day 30); (b) at or following completion of reinnervation (day 120); and (c) midway during the process of reinnervation (day 60). Messenger RNA is prepared from PCA muscles using standard methods known in the art. The RNA samples are hybridized to a cardiac muscle microarray chip developed at Vanderbilt University, which includes about 2,500 unique sequences from a dog cardiac muscle library.

REFERENCES

The references listed below as well as all references cited in the specification are incorporated herein by reference to the extent that they supplement, explain, provide a background for or teach methodology, techniques and/or compositions employed herein.

Al-Majed A A, Brushart T M & Gordon T (2000) Electrical Stimulation Accelerates and Increases Expression of BDNF and TRKB mRNA in Regenerating Rat Femoral Motoneurons. *Eur J Neurosci* 12:4381-4390.

Billante C R, Zealear D L, Courey M S & Nefterville J L (2002) Effect of Chronic Electrical Stimulation of Laryngeal Muscle on Voice. *Ann Otol Rhinol Laryngol* 111:328-332.

Brushart T M, Gerber J, Kessens P, Chen Y G & Royall R M (1998) Contributions of Pathway and Neuron to Preferential Motor Reinnervation. *J Neurosci* 18:8674-8681.

Di Giulio A M, Germani E, Lesma E, Muller E & Gorio A (2000) Glycosaminoglycans Co-Administration Enhance Insulin-Like Growth Factor-I Neuroprotective and Neuroregenerative Activity in Traumatic and Genetic Models of Motor Neuron Disease: A Review. *Int J Dev Neurosci* 18:339-346.

Evans G R (2000) Challenges to Nerve Regeneration. *Semin Surg Oncol* 19:312-318.

Gorman P H (2000) An Update on Functional Electrical Stimulation after Spinal Cord Injury. *Neurorehabil Neural Repair* 14:251-263.

Hall S (1997) Axonal Regeneration through Acellular Muscle Grafts. *J Anat* 190:57-71.

Insalaco G, Kuna S T, Cibella F & Villeponteaux R D (1990) Thyroarytenoid Muscle Activity During Hypoxia, Hypercapnia, and Voluntary Hyperventilation in Humans. *J Appl Physiol* 69:268-273.

Ludlow C L, Van Pelt F & Koda J (1992) Characteristics of Late Responses to Superior Laryngeal Nerve Stimulation in Humans. *Ann Otol Rhinol Laryngol* 101:127-134.

Politis M J (1985) Specificity in Mammalian Peripheral Nerve Regeneration at the Level of the Nerve Trunk. *Brain Res* 328:271-276.

Popovic M R, Curt A, Keller T & Dietz V (2001) Functional Electrical Stimulation for Grasping and Walking: Indications and Limitations. *Spinal Cord* 39:403-412.

Pototschnig C & Thumfart W F (1997) Electromyographic Evaluation of Vocal Cord Disorders. *Acta Otorhinolaryngol Belg* 51:99-104.

Rushton D N (1997) Functional Electrical Stimulation. *Physiol Meas* 18:241-275.

Sweeney P C, Lyons G M & Veltink P H (2000) Finite State Control of Functional Electrical Stimulation for the Rehabilitation of Gait. *Med Biol Eng Comput* 38:121-126.

U.S. Pat. No. 5,366,493
U.S. Pat. No. 5,480,416
U.S. Pat. No. 5,504,197
U.S. Pat. No. 5,562,707
U.S. Pat. No. 5,571,148
U.S. Pat. No. 5,690,692
U.S. Pat. No. 5,721,243
U.S. Pat. No. 5,897,579
U.S. Pat. No. 5,898,066
U.S. Pat. No. 5,983,140
U.S. Pat. No. 5,991,649
U.S. Pat. No. 6,029,090
U.S. Pat. No. 6,051,017
U.S. Pat. No. 6,123,658
U.S. Pat. No. 6,132,361
U.S. Pat. No. 6,132,387
U.S. Pat. No. 6,134,469
U.S. Pat. No. 6,163,725
U.S. Pat. No. 6,179,771
U.S. Pat. No. 6,214,021
U.S. Pat. No. 6,217,491
U.S. Pat. No. 6,226,552
U.S. Pat. No. 6,233,472
U.S. Pat. No. 6,243,607
U.S. Pat. No. 6,365,149

Zealear D L & Dedo H H (1977) Control of Paralysed Axial Muscles by Electrical Stimulation. *Acta Otolaryngol* 83:514-527.

Zealear D L, Rainey C L, Jerles M L, Tanabe T & Herzon G D (1994) Technical Approach for Reanimation of the Chronically Denervated Larynx by Means of Functional Electrical Stimulation. *Ann Otol Rhinol Laryngol* 103:705-712.

Zealear D L, Billante C L, Chongkolwatana C & Herzon G D (2000a) The Effects of Chronic Electrical Stimulation on Laryngeal Muscle Reinnervation. *ORL J Otorhinolaryngol Relat Spec* 62:87-95.

Zealear D L, Billante C R, Chongkolwatana C, Rho Y S, Hamdan A L & Herzon G D (2000b) The Effects of Chronic Electrical Stimulation on Laryngeal Muscle Physiology and Histochemistry. *ORL J Otorhinolaryngol Relat Spec* 62:81-86.

Zealear D L, Billante C R, Courey M S, Sant'Anna G & Netterville J L (2002). Electrically stimulated glottal opening combined with adductor muscle blockade restores both ventilation and voice in a patient with bilateral laryngeal paralysis. *Ann Otol Rhinol Laryngol* 111 (6):500-506.

Zealear D L, Rodriguez R J, Kenny T, Billante M J, Cho Y, Billante C R & Garren KC (2002) Electrical Stimulation of a Denervated Muscle Promotes Selective Reinnervation by Native over Foreign Motoneurons. *J Neurophysiol* 87:2195-2199.

It will be understood that various details of the invention can be changed without departing from the scope of the invention. Furthermore, the foregoing description is for the purpose of illustration only, and not for the purpose of limitation—the invention being defined by the claims appended hereto.

What is claimed is:

1. A method for promoting selective reinnervation of one or more denervated target muscles in a subject comprising:

stimulating one or more target muscles with a pattern of electrical, magnetic, or a combination of electrical and magnetic stimulatory activity selected to selectively enhance reinnervation of the one or more denervated target muscles by native neurons and inhibit reinnervation of the one or more denervated target muscles by foreign neurons;

wherein the pattern of stimulatory activity comprises a magnitude, frequency, and duration of stimulatory activity in the one or more denervated target muscles that is substantially similar to the magnitude, frequency, and duration of stimulatory activity in the one or more denervated target muscles prior to denervation, wherein the pattern of stimulating activity is tailored to a particular muscle;

wherein stimulating the one or more denervated target muscles comprises intermittently providing a stimulus to at least a portion of the one or more denervated target muscles and turning off the stimulus to the one or more denervated target muscles with a duty cycle of less than 10%, the one or more denervated target muscles being inactive when the stimulus is turned off; and removing the stimulus to the one or more denervated target muscles after function is restored to the one or more denervated target muscles.

2. The method of claim 1, wherein the one or more denervated muscles comprises a smooth muscle, a cardiac muscle, or a skeletal muscle.

3. The method of claim 2, wherein the skeletal muscle comprises a laryngeal muscle.

4. The method of claim 3, wherein the laryngeal muscle comprises a posterior cricoarytenoid muscle.

5. The method of claim 1, wherein promoting selective reinnervation of the one or more denervated target muscles in a subject comprises promoting selective reinnervation of one or more denervated target muscles in a mammal.

6. The method of claim 5, wherein promoting selective reinnervation of one or more denervated target muscles in a mammal comprises promoting selective reinnervation of a denervated target muscles in a human.

7. The method of claim 1, wherein the stimulating comprises providing electrical stimulation.

8. The method of claim 1, wherein the stimulating comprises providing magnetic stimulation.

9. The method of claim 1, further comprising providing a stimulator in proximity to the one or more denervated target muscles, whereby the one or more denervated muscles is stimulated by the stimulator.

10. The method of claim 9, wherein the stimulator is implantable or injectable.

11. The method of claim 9, wherein the stimulator is programmable.

12. The method of claim 1, wherein the native neurons comprise motoneurons, and wherein the foreign neurons comprise motoneurons.

13. The method of claim 1, further comprising restoring function of the one or more denervated target muscles.

14. The method of claim 13, wherein the function of the one or more target muscles comprises contraction.

15. The method of claim 1, further comprising evaluating the quality and magnitude of reinnervation of the one or more target muscles following stimulation.

16. The method of claim 1, wherein stimulating the one or more target muscles comprises stimulating reconnecting neurons within the one or more target muscles.

17. The method of claim 1, wherein the one or more target muscles comprises a slow contracting muscle; and
    wherein the frequency of stimulation is less than a frequency that produces tetanization.

18. The method of claim 17, wherein the frequency of stimulation is less than a frequency of about 10 pulses per second.

19. The method of claim 1, wherein the one or more target muscles comprises a fast contracting muscle; and
    wherein the frequency of stimulation is greater than a frequency of about 50 pulses per second.

20. The method of claim 1, wherein stimulating the one or more target muscles comprises sequentially stimulating a plurality of discrete stimulation sites on the one or more target muscles.

21. A method for promoting selective reinnervation of one or more denervated target muscles in a subject comprising:
    stimulating the one or more target muscles with a pattern of electrical, magnetic, or a combination of electrical and magnetic stimulatory activity selected to selectively enhance reinnervation of the one or more denervated target muscles by native neurons and inhibit reinnervation of the one or more target muscles by foreign neurons, wherein the pattern of stimulating activity is tailored to a particular muscle; and
    removing the stimulatory activity to the one or more target muscles after function is restored to the one or more target muscles;
    wherein stimulating the one or more denervated target muscles is initiated during a six-month period following denervation of the one or more denervated target muscles in which spontaneous reinnervation of the one or more denervated target muscles may occur; and
    wherein stimulating the one or more denervated target muscles comprises intermittently providing a stimulus to at least a portion of the one or more denervated target muscles and turning off the stimulus to the one or more denervated target muscles with a duty cycle of less than 10%, the one or more denervated target muscles being inactive when the stimulus is turned off.

* * * * *